United States Patent
Roh et al.

(10) Patent No.: US 10,130,670 B2
(45) Date of Patent: Nov. 20, 2018

(54) COMPOSITION FOR TREATING OR PREVENTING INFLAMMATORY SKIN DISEASE, COMPRISING, AS ACTIVE INGREDIENT, IMMATURE CITRUS FRUIT EXTRACT, OR SYNEPHRINE OR SALT THEREOF

(71) Applicant: BIO SPERCTRUM, INC., Seongnam-si, Gyeonggi-Do (KR)

(72) Inventors: Kyung Baeg Roh, Seongnam-si (KR); Young Soo Kim, Seoul (KR); Eun Sun Jung, Suwon-si (KR); Deok Hoon Park, Seongnam-si (KR)

(73) Assignee: BIOSPECTRUM, INC., Yongin-si, Gyeonggi-Do (KR)

( * ) Notice: Subject to any disclaimer, the term of this patent is extended or adjusted under 35 U.S.C. 154(b) by 517 days.

(21) Appl. No.: 14/902,512

(22) PCT Filed: Jun. 19, 2014

(86) PCT No.: PCT/KR2014/005403
§ 371 (c)(1),
(2) Date: Dec. 31, 2015

(87) PCT Pub. No.: WO2015/002393
PCT Pub. Date: Jan. 8, 2015

(65) Prior Publication Data
US 2016/0375079 A1  Dec. 29, 2016

(30) Foreign Application Priority Data
Jul. 3, 2013 (KR) ................. 10-2013-0077877

(51) Int. Cl.
*A61K 36/00* (2006.01)
*A61K 36/752* (2006.01)
*A61K 31/137* (2006.01)
*A61K 9/06* (2006.01)
*A61K 9/20* (2006.01)
*A61K 9/14* (2006.01)

(52) U.S. Cl.
CPC .............. *A61K 36/752* (2013.01); *A61K 9/06* (2013.01); *A61K 9/148* (2013.01); *A61K 9/20* (2013.01); *A61K 31/137* (2013.01)

(58) Field of Classification Search
CPC ..................................................... A61K 36/00
USPC ........................................................ 424/725
See application file for complete search history.

(56) References Cited

FOREIGN PATENT DOCUMENTS

| JP | 2005132791 A | 5/2005 |
| JP | 2005132792 A | 5/2005 |
| KR | 20000046630 A | 7/2000 |
| KR | 20120035741 A | 4/2012 |

OTHER PUBLICATIONS

International Search Report dated Sep. 22, 2014 for PCT/KR2014/005403 and English translation.

*Primary Examiner* — Michael V Meller
(74) *Attorney, Agent, or Firm* — Lucas & Mercanti, LLP

(57) ABSTRACT

The present invention relates to a composition for treating or preventing an inflammatory skin disease, comprising, as an active ingredient, an unripe *Citrus unshiu* fruit extract and/or Synephrine or salt thereof. The composition of the present invention prevents an inflammatory reaction by inhibiting activity of STAT6, expression of eotaxin-1 and an agglomeration function of eosinophil, and thus, shows effects of preventing and treating an allergic inflammatory disease, atopic dermatitis, eczema, psoriasis, etc. Also, the composition of the present invention does not have cytotoxicity and a skin side effect, and thus, can be safely applied to pharmaceutical products and cosmetics.

1 Claim, 6 Drawing Sheets

COMPOSITION FOR TREATING OR PREVENTING INFLAMMATORY SKIN DISEASE, COMPRISING, AS ACTIVE INGREDIENT, IMMATURE CITRUS FRUIT EXTRACT, OR SYNEPHRINE OR SALT THEREOF

CROSS-REFERENCE TO RELATED APPLICATIONS

This application is a 371 of PCT/KR2014/005403, filed Jun. 19, 2014, which claims the benefit of KR Patent Application No 10-2013-0077877, filed Jul. 3, 2013, the contents of each of which are incorporated herein by reference.

TECHNICAL FIELD

The present invention is a result of a research subject (Project Number: A103017) regarding materials for improving inflammatory skin disease by National Coordinating Center for Global Cosmetics R&D of Ministry of Health and Welfare of Republic of Korea, and specifically relates to a composition for treating or preventing inflammatory skin disease, comprising, as an active ingredient, unripe citrus fruit extract, or Synephrine or salt thereof.

BACKGROUND ART

Atopic dermatitis is a chronic inflammatory skin disease characterized in a persistent Pruritus and acute and chronic eczematous lesion of skin and may be accompanied by asthma, Allergic rhinitis and the like, in addition to the lesion of skin. As a cause of atopic dermatitis, skin barrier abnormality, etc., greatly except for a genetic factor, immunological factor and environmental factor, is recently considered as a major cause. In addition, it has been reported that atopic dermatitis is occurred by a lack of γ-linolenic acid in lipid and by a secretion of cytokine or chemokine.

Chemokine plays an important role in inflammatory cell infiltration in skin, and eotaxin-1, being C-C chemokine, is particularly increased in such a lesion of dermatitis, which is closely related to chemotaxis of eosinophil having C-C chemokine receptor 3 (CCR3) and Helper-T cell Type 2 (Th2).

Eotaxin-1 is expressed on various kinds of cells such as eosinophil, lymphocyte, macrophage, fibroblast, smooth muscle cell, epithelial cell, and the like, and plays an important role in attracting eosinophil into a lesion of dermatitis. Since eosinophil secretes a proteinous radical which has a very strong toxicity and a free radical, it can kill microorganisms and parasites, but if it is improperly activated, it can cause serious tissue damage and thus should be regulated very strictly. When such eosinophil moves from circulating blood to the tissue, the key material is eotaxin-1, and eotaxin-1 secreted from tissues of inflammatory region binds to CCR3 receptor on a surface of eosinophil to achieve the movement of eosinophil to inflammatory lesion. Therefore, the skin inflammatory reaction can be prevented by effectively regulating an expression of eotaxin-1 and CCR3.

Atopy is one of the important diseases mainly emerged in the advanced country since the 1970's, and is a growing trend all around of world and has a report that a prevalence rate thereof is 20% of the population of the world. There are 1.5 million of people having atopy in U.S.A. and 16.3% of elementary/middle/high school students have atopy in Korea. (Ahn S. Y. et al., *J. Skin Barrier Res.*, 8, 47-51, 2006).

At present, a steroid agent, topical immunosuppressive drug, anti-histamine agent, and the like are used as a medicine of atopic dermatitis, but when the above drugs are used for a long time, since there are problems such as thinning of the skin, discoloration of the skin color, osteoporosis, sclerosis of the arteries, possibility of carcinogenesis, worsening symptoms due to a resistance and the like, the development of the composition having an excellent anti-inflammation effect, while being safety because of the deriving thereof from a natural substance, is being made.

Meanwhile, *Citrus unshiu* is an evergreen tree of *Citrus* genus, Rutaceae family, and reseeds in Jeju-island in Korea, and is known to widely distribute in Japan, China, Latin America, the Black see, and the like. A fruit of Citrus tree is edible itself as well as 20% or more of it is consumed as a processing product such as juice, canned foods, and the like, and has plentiful fruit juice, unique flavor and high functional ingredients. For example, citrus contains materials such as d-limonene, linalool, linalylacetate as sesame flavor, hesperidin, naringin, poncirin, nobiletin as flavonoid, Synephrine, pectin, ascorbic acid, beta-cryptoxanthin, courin as alkaloid, and the like, and they are known to have stimulation of digestive organs, obesity, cough, blood-pressure-rising, anti-allergic, antimicrobial function, and the like.

But, a price of Citrus has been decreased sharply because of the unripe Citrus fruit and shipping of Citrus lowered in the quality due to the environmental changes such as the recent frequent rains, moisture, temperature, and the like, the mass-production via a protected cultivation such as a greenhouse and preference for imported citrus. Therefore, in order to reduce amounts of production of Citrus and gentrify the quality of Citrus, countermeasures such as in-advance harvest for unripe Citrus and the treatment, a thorough selection and quality control for Citrus, and development of a functional composition by using unripe Citrus has been prepared. As one example, many studies for isolating biological active substances from the unripe Citrus in-advance harvested or development of use by using them, are being made.

As the techniques related to the above, Korean Registered Patent No. 1259791 discloses a method for manufacturing a health supplement food by using Citrus flavonoid contained in an unripe Citrus and the health supplement food using it, Korean Registered Patent No. 1162761 discloses a composition for preventing or treating obesity comprising an unripe Citrus extract, and Korean Registered Patent No. 01315212 discloses an antidepressant containing the extract isolated from an unripe citrus pericarp of *Citrus unshiu* tree.

Therefore, inventors of the present invention studied the utilization plan for unripe Citrus fruit, found that the unripe Citrus fruit extract and synephrine have an excellent effect in treating an inflammatory skin disease and then have completed the present invention.

DISCLOSURE

Technical Problem

DETAILED DESCRIPTION OF THE INVENTION

An object of the present invention is to provide a composition for treating or preventing inflammatory skin disease, comprising, as an active ingredient, an unripe *Citrus unshiu* fruit extract and/or synephrine or salt thereof.

Another object of the present invention is to provide a cosmetic composition for improving or preventing inflammatory skin disease, comprising, as an active ingredient, unripe *Citrus unshiu* fruit extract and/or synephrine or salt thereof.

Technical Solution

As one embodiment, the present invention relates to a composition for treating or preventing inflammatory skin disease, comprising, as an active ingredient, an unripe *Citrus unshiu* fruit extract.

In the present invention, *Citrus unshiu* is an evergreen tree of *Citrus* genus, Rutaceae family, and the unripe *Citrus unshiu* fruit means the unripe fruit lasted for 3 to 4 months after forming the fruit.

The unripe fruit may have a change in the contained ingredients according to the period lasted after forming the fruit, the unripe *Citrus unshiu* fruit of the present invention is characterized in containing synephrine. In the specific experiments, inventors of the present invention firstly found that the unripe *Citrus unshiu* fruit extract lasted for 3 to 4 months after forming the fruit contains synephrine unlike extracts of other unripe citrus fruits.

Accordingly, the unripe *Citrus unshiu* fruit extract of the present invention is characterized in containing synephrine.

The unripe *Citrus unshiu* fruit extract of the present invention comprises all extracts, fractions and refinings obtained from the respective steps of extraction, fractionation or purification by using any one or more selected from the groups consisting of fruit pericarp, fruit flesh and fruit of the unripe *Citrus unshiu* fruit, the diluents, concentrate or dry matter thereof.

In the present invention, the extract can be obtained by using the extraction method and extracted solvent known in the art. Preferably, it can be obtained by using water, dry or hydrous lower alcohol (methanol, ethanol, propanol, butanol, etc.), the mixed solvent of the lower alcohol and water, acetone, ethyl acetate, chloroform or 1,3-butyleneglycol, as the extraction solvent.

In addition, the unripe *Citrus unshiu* fruit extract can be obtained through the conventional purification procedure except for the extraction method by the extraction solvent. For example, unripe *Citrus unshiu* fruit extract can be obtained via fractions obtained by various purification methods additionally performed such as a separation by using ultrafiltration having constant molecular weight cut-off value, a separation by various chromatographies (that prepared for the separation according to a size, charge, hydrophobicity or affinity), and the like.

In the present invention, the inflammatory skin disease refers to skin troubles or skin diseases occurred via various routes such as allergic inflammatory disease, atopic dermatitis, skin eczema, psoriasis, etc.

As one specific practice, as a result of inducing eotaxin-1 by treating interleukin-4 (IL-4) on the normal fibroblast (NIH/3Ts) and then reviewing mRNA of eotaxin-1 and the expression inside/outside of cells according to a concentration of the unripe *Citrus unshiu* fruit extract, there appeared a trend that as the concentration of the unripe *Citrus unshiu* fruit extract is increased, the mRNA and expression inside/outside of cells is increased. Also, as a result of testing the effect for improving atopic inflammation by using cream comprising the unripe *Citrus unshiu* fruit extract, it was identified that it is safe on a human skin, and the longer hours of use of it, the better atopic inflammation becomes.

Accordingly, the unripe *Citrus unshiu* fruit extract of the present invention can be usefully used for treating or preventing of inflammatory skin diseases such as allergic inflammation disease, atopic dermatitis, skin eczema or psoriasis, etc. In addition, the unripe *Citrus unshiu* fruit is edible, and as a result of identifying the safety through the identification experiment of the extract to the human body, it can be safely used in the human body.

The unripe *Citrus unshiu* fruit extract of the present invention is comprised in the composition of the present invention in an amount of 0.0001 to 10% by weight, preferably 0.0001 to 5% by weight relative to the weight of total composition. When the weight of the unripe *Citrus unshiu* fruit extract is less than 0.0001% by weight, the efficacy of the anti-inflammation activity is weak, and when it is greater than % by weight, there is a problem that the safety in a formulation is not secured since an increase of the effect according to the increase of the content of the unripe *Citrus unshiu* fruit extract is very weak.

As another embodiment, the present invention relates to a composition for treating or preventing an inflammatory skin disease, comprising, as an active ingredient, synephrine or salt thereof.

In the present invention, the synephrine is a material having IURAC name of 4-[1-hydroxy-2-(methylamino) ethyl]phenol(4-[1-hydroxy-2-(methylamino)ethyl]phenol), and its structure is represented by the below chemical formula 1:

[Chemical formula 1]

The synephrine is known as having an efficacy for anti-cancer, depression and obesity, and can be those extracted, separated and purified from *Citrus* genus, *Fortunella margarita* genus, and trifoliolate orange genus, belonging to *Citrus*, preferably *Citrus unshiu*, more preferably, the unripe citrus fruit extract of *Citrus unshiu*; various organs, roots, stems, leaves, fruits, flowers of the natural, hybrid and variant plants as well as products obtained or chemically synthesized through culturing microorganisms such as *Saccharomyces cerevisiae*, etc. (for example, (±)-synephrine of Sigma).

In the present invention, acid additional salts formed by a free acid or metal salts formed by a base are useful as the salts of synephrine. As one example, the free acid can use an inorganic acid and organic acid, and the inorganic acid can use hydrochloric acid, sulfuric acid, bromic acid, sulfurous acid or phosphoric acid, and the organic acid can use citric acid, acetic acid, maleic acid, fumaric acid, gluconic acid, methanesulfonic acid, etc. In addition, as a metal salt, alkaline metal salt or alkaline earth metal salt, sodium, potassium or calcium salts can be used. But, it is not limited to them.

In one specific practice, as a result of inducing eotaxin-1 by treating interleukin-4 (IL-4) on the normal fibroblast (NIH/3Ts) and then reviewing mRNA of eotaxin-1 and the expression inside/outside of cells according to a concentration of synephrine, there appeared a trend that as the concentration of synephrine is increased, mRNA and expression inside/outside of cells is increased. Also, as a result of testing the effect for improving atopic inflammation by using cream comprising synephrine, it was identified that it is safe on a human skin, and the longer hours of use of it, the better atopic inflammation becomes.

Accordingly, synephrine of the present invention and salt thereof can be usefully used for treating or preventing of inflammatory skin diseases such as allergic inflammation disease, atopic dermatitis, skin eczema or psoriasis, etc. In addition, as a result of identifying the safety through the identification experiment of synephrine or salt thereof to the human body, it can be safely used in the human body.

The synephrine or salt thereof is comprised in the composition of the present invention in an amount of 0.0001 to 10% by weight, preferably 0.0001 to 5% by weight relative to the weight of total composition. When the weight of synephrine or salt thereof is less than 0.0001% by weight, the efficacy of the treatment and prevention for the inflammatory skin disease is weak, when it is greater than 10% by weight, there is a problem that the safety in a formulation is not secured since an increase of the effect according to the increase of the content of synephrine or salt thereof is very weak.

Meanwhile, the composition of the present invention for treating or preventing an inflammatory skin disease, comprising, as an active ingredient, the unripe *Citrus unshiu* fruit extract and/or the composition for treating or preventing an inflammatory skin disease, comprising, as an active ingredient, synephrine can be available as a pharmaceutical composition.

The pharmaceutical composition can comprise a pharmaceutically acceptable carriers, excipients and diluents, in addition to the composition for treating or preventing an inflammatory skin disease, comprising, as an active ingredient, the unripe *Citrus unshiu* fruit extract and/or the composition for treating or preventing an inflammatory skin disease, comprising, as an active ingredient, synephrine or salt thereof. The pharmaceutical composition of the present invention comprises the ingredients commonly used in the pharmaceutical composition. As one example, it can comprise lubricant, wetting agent, sweetening agent, flavoring agent, emulsifying agent, preserving agent and carrier.

The carrier suitable for the pharmaceutical composition includes, but not limited to, lactose, dextrose, sucrose, sorbitol, mannitol, starch, acacia gum, calcium phosphate, alginate, gelatin, calcium silicate, microcrystalline cellulose, polyvinylpyrrolidone, celloluse, water, syrup, methyl cellulose, methylhydroxybenzoate, prophylhydroxybenzoate, talc, stearic acid, magnesium, mineral oil, and the like. The suitable pharmaceutically acceptable carrier or agents are specifically disclosed in, for example, Remington's Pharmaceutical Sciences (19$^{th}$ ed., 1995).

The pharmaceutical composition can be administered orally or parenterally, and can be applied, preferably, by parenteral administration, more preferably in the manner of topical application by application.

The pharmaceutical composition can be administered in the pharmaceutically effective amount. The pharmaceutically effective amount in the present invention means one sufficient to treat or prevent the disease in the rational benefit/risk rate applicable to the medical treatment or prevention, and the effective dose level can be determined by the kinds of disease and severity thereof, activity of the drug, age, weight, health and sex of a patient, sensitivity of the patient to the drug, the administration hours of the specific extract used, the administration route and excretion rate, the treatment period, the combination with the specific extract used or factor including the co-administered drug and other factors well known in the medical field. Generally, a dosage of 0.1 to 1000 mg/kg/day, preferably 10 to 100 mg/kg/day can be administered to an adult, one time to several times per day. In addition, in the case of external preparation, it is preferable to continuously use it in the amount of 1.0 to 3.0 ml by applying 1 to 5 times per day for 1 month. But, the administration amount is not intended to limit the scope of the present invention.

The pharmaceutical composition can be prepared as unit dose form by manufacturing the preparation by using the pharmaceutically acceptable carriers and/or excipients or can be prepared by entering into a multi-dose container, according to the method easily practiced by an ordinary person in the art to which the present invention subjects. In this case, the formulation can be formulated as a common preparation in the pharmaceutics according to the object of the treatment, and it can be formulated into tablet, capsule, powder, granule, suspension, emulsion, syrup, turbid fluid, plaster, ointment, spray, oil agent, gel agent, sprit, tincture, bathing agent, liniment, lotion, patch, pad agent, cream, etc. In addition, it can be preferably used as a skin external preparation having the object for topical administration by directly applying to the affected area, and in this case, the form of ointment, lotion, spray, gel, etc. is preferable. Such skin external preparation can also be included in the support base or matrix, etc. which can be directly applied to the treating site, and the example of the support base includes gauze or bandage.

The composition for treating or preventing an inflammatory skin disease, comprising, as an active ingredient, the unripe *Citrus unshiu* fruit extract and/or the composition for treating or preventing an inflammatory skin disease, comprising, as an active ingredient, synephrine or salt thereof can be available as a cosmetic composition.

The cosmetic composition comprises the ingredients commonly used in the cosmetic composition, in addition to the composition for treating or preventing an inflammatory skin disease, comprising, as an active ingredient, the unripe *Citrus unshiu* fruit extract and/or the composition for treating or preventing an inflammatory skin disease, comprising, as an active ingredient, synephrine or salt thereof. For example, it comprises the conventional adjuvant such as antioxidant, stabilizing agent, dissolving agent, vitamin, pigment and flavor agent, and the carrier.

The cosmetic composition can be formulated into solution, suspension, emulsion, paste, gel, cream, lotion, powder, soap, surfactant-containing cleansing, oil, powder foundation, emulsion foundation, wax foundation, spray, nourishing cream, astringent, soft floral water, lotion, essence, nutritional gel, or massage cream, etc., but it is not limited to those.

When the formulation of the cosmetic composition is the paste, cream or gel, animal oil, vegetable oil, wax, paraffin, starch, tragacanth, cellulose derivative, polyethylene glycol, silicone, bentonite, silica, talc or zinc oxide, etc. can be used as the carrier ingredient.

When the formulation of the cosmetic composition is the powder or spray, the lactose, talc, silica, aluminum hydroxide, calcium silicate or polyamide powder can be utilized, and in particular when it is the spray, a propellant such as chlorofluorohydrocarbon, propane/butane or dimethyl ether can be additionally included.

When the formulation of the cosmetic composition is the solution or turbid fluid, the solvent, solubilizing agent or emulsifying agent can be utilized as a carrier ingredient, and for example, water, ethanol, isopropanol, ethyl carbonate, ethyl acetate, benzyl alcohol, benzyl benzoate, propylene glycol, 1,3-buthylglycol oil, glycerol aliphatic ester, polyethylene glycol or aliphatic ester of sorbitan, etc. can be utilized as the carrier ingredient.

When the formulation of the cosmetic composition is suspension, the liquid diluents such as water, ethanol or propylene glycol, suspending agent such as ethoxylated isostearyl alcohol, polyoxyethylene sorbitol ester and polyoxyethylene sorbitan ester, microcrystalline cellulose, aluminum metahydroxide, bentonite, agar, or tragacant, etc. can be utilized as the carrier ingredient.

When the formulation of the cosmetic composition is the surfactant-containing cleansing, the aliphatic alcohol sulfate, aliphatic alcohol ether sulfate, sulphosuccinic monoester, isethionate, imidazolinium derivative, methyltaurate, sarcosinate, fatty acid amide ether sulfate, alkylamidobetaine, aliphatic alcohol, fatty acid glyceride, fatty acid diethanolamide, vegetable oil, lanoline derivative or ethoxylated glycerol fatty acid ester, etc. can be utilized as the carrier ingredient.

As another embodiment, the present invention relates to the method for treating, improving or preventing the inflammatory skin disease of a subject by administering the composition comprising, as an effective ingredient, unripe *Citrus unshiu* fruit extract, and/or Synephrine or salt thereof to the subject.

The composition administered to the subject of the present invention has the effect for treating, improving or preventing the inflammatory skin disease, for example, allergic inflammatory disease, atopic dermatitis, skin eczema, psoriasis, and the like, as mentioned above.

The term, "subject" in the present invention means a mammal such as monkey, cow, horse, pig, sheep, dog, cat, rat, mouse, chimpanzee, etc., including human, having the disease symptom of which can be alleviated by administering the composition of the present invention.

In the present invention, the term, "treatment" or "improvement" means (a) an inhibition of a development of disease or disorder, (b) an alleviation of the disease or disorder and (c) a removal of the disease or disorder. In the present invention, the term, "prevention" means the inhibition of an occurrence of the disease or disorder in the subject who did not diagnosed having the disease or disorder, but has the tendency of being liable to such disease or disorder.

Advantageous Effects

The composition for treating or preventing inflammatory skin disease prevents the inflammatory reaction by inhibiting STAT6 activity, an expression of eotaxin-1, an agglomeration of eosinophil, and thus exhibit the prevention or treatment effect for allergic inflammation disease, atopic dermatitis, skin eczema, psoriasis, etc. Therefore, the composition comprising, as an effective ingredient, unripe *Citrus unshiu* fruit extract and/or synephrine or salt thereof can be safely applied to the medicine and cosmetics.

BEST MODE FOR INVENTION

Hereinafter, the present invention will be given in detail through Examples. The Examples is given only to more specifically describe the present invention, and it will be self-evident to the ordinary person in the art to which the present invention subject that the scope of the present invention is not limited to such Examples.

Example 1: The Preparation of Unripe *Citrus unshiu* Fruit Extract

The unripe *Citrus unshiu* was washed and pulverized, and then, immersed into ethanol for five days and extracted. Then, it was filtrated and concentrated, and then lyophilized to prepare the unripe *Citrus unshiu* fruit extract.

Example 2: Isolation and Analysis of Synephrine from the Unripe *Citrus unshiu* Fruit The unripe *Citrus unshiu* fruit extract obtained from the Example 1 was purified by Bulk C18 chromatography, was divided into eleven (11) fractional extracts, and then new active ingredient material was isolated from the second fraction via C18 column chromatography using Prep-HPLC. The structure for the active ingredient material was identified as being 4-[1-hydroxy-2-(methylamino)ethyl]phenol (molecular weight: 167.21) by using an instrument such as NMR, IR, UV, etc., and the general chemical name thereof was identified as synephrine.

Figure 1:
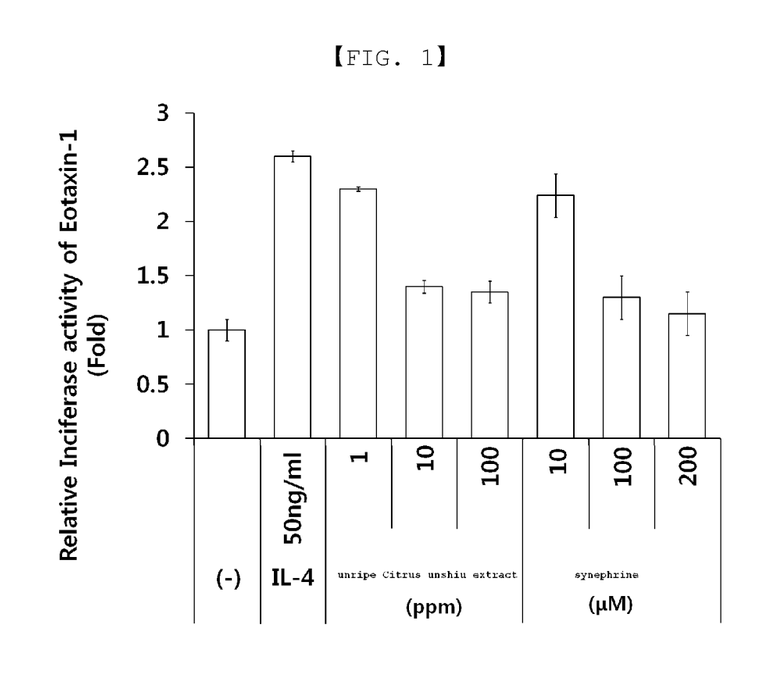
FIG. 1 is a result determining the effect for inhibiting the expression of eotaxin-1 inside of the cell depending on the concentration of the unripe *Citrus unshiu* fruit extract or synephrine isolated from it.

Example 3: Determination of the Effect Inhibiting the Intracellular Secretion of Eotaxin-1 by the Unripe *Citrus unshiu* Fruit Extract or Synephrine Isolated from It Human normal fibroblast (human normal fibroblast, NIH/3T3, department of dermatology in Aju University) was transformed by inserting Eotaxin-1 reporter gene into it with superfect (Quigen Co.), and then cultured in 5% concentration of $CO_2$ cultivator under the condition of 37° C. for 24 hours. And then, the transformed fibroblast was inoculated into 24-well microplate with DMEM media so as to be about $2 \times 10^5$ cells per well, and treated with 1, 10, 100 ppm of unripe *Citrus unshiu* fruit extract, or 10, 100 and 200 μM of synephrine, respectively and then was treated simultaneously with 50 ng/ml of interleukin-4 (R&D, Minneapolis Minn., IL-4) known to induce eotaxin-1, cultivated for 24 hours to collect cells. Then, the collected cells were crushed and reacted with a substrate of luciferase to determine luminescence, and a promoter activity of eotaxin-1 was determined. The results are represented in FIG. 1.

As a result of the test, it was shown that the promoter activity of eotaxin-1 derived by IL-4 was reduced by the unripe *Citrus unshiu* fruit extract and synephrine isolated from it, and there is a concentration-dependent tendency when considering that as the concentration of the unripe *Citrus unshiu* fruit extract and synephrine isolated from it is increased, the promoter activity of eotaxin-1 is decreased accordingly.

Figure 2:
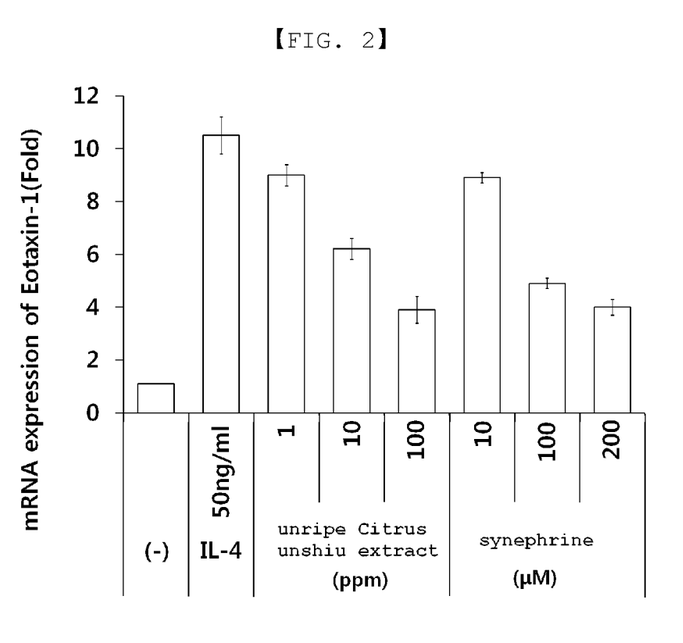
FIG. 2 is a result determining the effect for inhibiting the expression of eotaxin-1 outside of the cell depending on the concentration of the unripe *Citrus unshiu* fruit extract or synephrine isolated from it.

Example 4: Determination of the Effect Inhibiting the Extracellular Secretion of Eotaxin-1 by the Unripe *Citrus unshiu* Fruit Extract or Synephrine Isolated from It Human normal fibroblast (human normal fibroblast, NIH/3T3, department of dermatology in Aju University) was inoculated into 24-well microplate with DMEM media so as to be about $2\times10^5$ cells per well, and cultured in 5% concentration of $CO_2$ cultivator under the condition of 37° C. for 24 hours. And then, it was treated with 1, 10, 100 ppm of unripe *Citrus unshiu* fruit extract, or 10, 100 and 200 µM of synephrine, respectively and then was treated simultaneously with 50 ng/ml of interleukin-4 (R&D, Minneapolis Minn., IL-4), cultivated for 24 hours to collect cell culture media. And then, the degree of secretion of eotaxin-1 was determined by using ELISA kit. The results are represented in FIG. 2.

As a result of the test, it was appeared that the extracellular secretion of eotaxin-1 derived by IL-4 was reduced by the unripe *Citrus unshiu* fruit extract and synephrine isolated from it, and there is a concentration dependent tendency when considering that the more the concentration of the unripe *Citrus unshiu* fruit extract and synephrine isolated from it are increased, the more promoter activity of eotaxin-1 is decreased.

Figure 3:
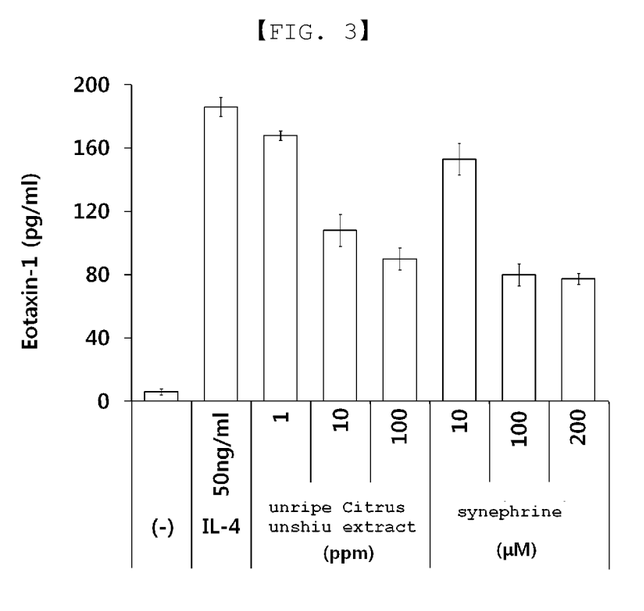
FIG. 3 is a result determining the effect for inhibiting the expression of eotaxin-1 mRNA depending on the concentration of the unripe *Citrus unshiu* fruit extract or synephrine isolated from it.
Figure 4:
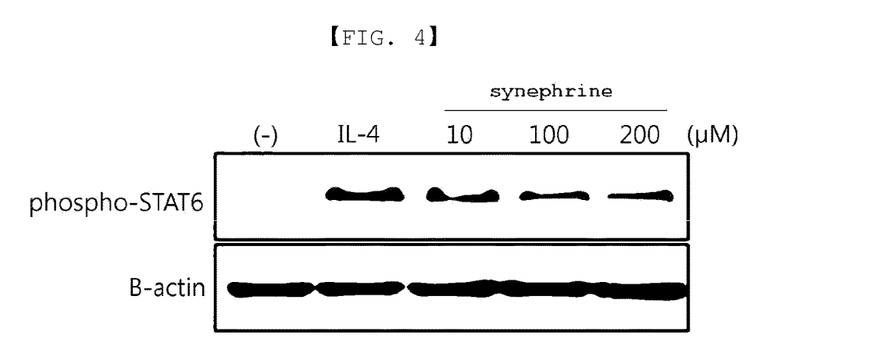
FIG. 4 is a result determining the effect for inhibiting phosphorylation of STAT6 depending on the concentration of synephrine isolated from the unripe *Citrus unshiu* fruit extract.

Example 5: Determination of the Effect Inhibiting the Expression of Eotaxin-1 mRNA by the Unripe *Citrus unshiu* Fruit or Synephrine Isolated from It Human normal fibroblast (human normal fibroblast, NIH/3T3, department of dermatology in Aju University) was inoculated into 24-well microplate with DMEM media to be about $2\times10^5$ cell per well, and cultured in 5% concentration of $CO_2$ cultivator under 37° C. for 24 hours. And then, it was treated with 1, 10, 100 ppm of unripe *Citrus unshiu* fruit extract, or 10, 100 and 200 µM of synephrine, respectively and then was treated simultaneously with 50 ng/ml of interleukin-4 (R&D, Minneapolis Minn., IL-4), cultivated for 24 hours to collect cell culture media. After extracting tRNA from the collected cells, a complementary DNA (cDNA) was synthesized based on the extracted tRNA and then, a quantitative Real-time PCR was performed by using the synthesized complementary DNA as a template to determine the degree of expression for mRNA of eotaxin-1. The results are represented in FIG. 3.

As a result of the test, it was shown that the expression of mRNA of eotaxin-1 derived by IL-4 was reduced by the unripe *Citrus unshiu* fruit extract and synephrine isolated from it, and there is a concentration-dependent tendency when considering that as the concentration of the unripe *Citrus unshiu* fruit extract and synephrine isolated from it are increased, expression of mRNA of eotaxin-1 is decreased, accordingly.

Example 6: Determination of the Effect Inhibiting STAT6 Phosphorylation of Synephrine Isolated from the Unripe *Citrus unshiu* Fruit Extract or Synephrine Isolated from It Human normal fibroblast (human normal fibroblast, NIH/3T3, department of dermatology in Aju University) was inoculated into 24-well microplate with DMEM media so as to be about $2\times10^5$ cells per well, and cultured in 5% concentration of $CO_2$ cultivator under the condition of 37° C. for 24 hours. And then, it was treated with 10, 100, 200 ppm of synephrine for 60 minutes, respectively and then 50 ng/ml of IL-4 was treated to cultivate for 20 minutes. Then, the cells were collected to dissolve and then determine the degree of phosphorylation inhibition of STAT6 through Western blot. The results are represented in FIG. 3.

As a result of the test, it was observed that synephrine effectively inhibits phosphorylation of STAT6 derived by IL-4.

Figure 5:
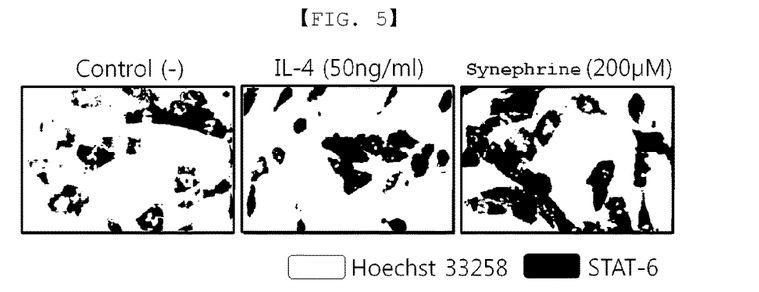
FIG. 5 is a result determining the effect for masking translocation of STAT6 into nucleus depending on the concentration of synephrine isolated from the unripe *Citrus unshiu* fruit extract.

Example 7: Determination of the Effect Inhibiting the Translocation of STAT6 into the Nucleus by Synephrine Isolated from the Unripe *Citrus unshiu* Fruit Extract Human normal fibroblast (human normal fibroblast, NIH/3T3, department of dermatology in Aju University) was inoculated into 24-well microplate with DMEM media so as to be about $2\times10^5$ cells per well, and cultured in 5% concentration of $CO_2$ cultivator under the condition of 37° C. for 24 hours. And then, it was treated with 200 µM of synephrine for 60 minutes, respectively and then was treated with 50 ng/ml of IL-4 to cultivate for 24 hours. And then, the cells was immobilized with paraformaldehyde (PFA) and treated with the primary antibody specifically reacting with STAT6. Then, it was treated with the second antibody attached by FITC to label the part reacting with STAT6 with a fluorescent material, and the nucleus was stained by using Hoechst and then, the translocation of STAT6 into the nucleus was observed with a confocal microscopy. The results are represented in FIG. 5.

As a result of the test, it was observed that synephrine inhibits the translocation of STAT6 derived by IL-4 into the nucleus.

Figure 6:
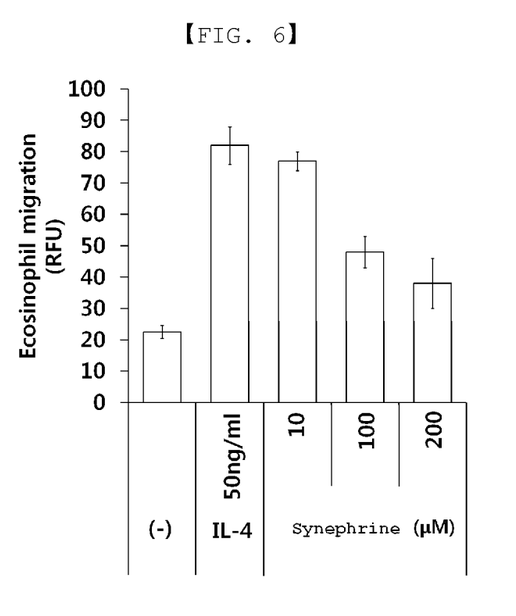
FIG. 6 is a result determining the effect for inhibiting the agglomeration of eosinophil depending on the concentration of synephrine isolated from the unripe *Citrus unshiu* fruit extract.

Example 8: Determination of the Effect Inhibiting the Eosinophil Agglomeration of Synephrine Isolated from the Unripe *Citrus unshiu* Fruit Extract Human normal fibroblast (human normal fibroblast, NIH/3T3, department of dermatology in Aju University) was inoculated into 24-well co-cultivation plate with DMEM media so as to be about $2\times10^5$ cells per well, and cultured in 5% concentration of $CO_2$ cultivator under the condition of 37° C. for 24 hours. And then, it was treated with 10, 100 and 200 µM of synephrine for 60 minutes, respectively and then 50 ng/ml of IL-4 was treated to induce the expression of eotaxin-1. Simultaneously, eosinophil was inoculated and cultivated for 24 hours. After the cultivation, the transmigration degree of eosinophil moved through the membrane to bottom of the plate was determined. The determination was measured via a fluorescence staining by using CytoSelect™ 24-Well Cell Migration Assay kit (Cell biolabs, INC., USA). The results are represented in FIG. 6.

As a result of the test, it was identified that synephrine inhibits the movement of eosinophil derived by eotaxin-1 expressed from the treatment of IL-4.

Example 9: Test for Identifying the Safety of Synephrine Isolated from the Unripe *Citrus unshiu* Fruit Extract to the Human Skin In order to identify as to whether the unripe *Citrus unshiu* fruit extract or synephrine isolated from the unripe *Citrus unshiu* fruit is safe or not, the skin external preparation based on squalene wherein 1, 10 and 100 ppm of the unripe *Citrus unshiu* fruit extract prepared in Example 1 were added, was prepared, and the skin external preparation wherein 10, 150 and 300 ppm of synephrine of Example 2 were added, were prepared, respectively.

Then, the skin external preparations were applied as a patch to areas of humerus of 30 adults for accumulated 24 hours on alternate day in total 9 times to test as to whether synephrine stimulates the skin. The control used the skin external preparation based on squalene wherein the unripe *Citrus unshiu* fruit extract or synephrine was not comprised.

The patch used Finn chamber (Epitest Ltd, Filand) and the patch was practiced after dropping with 15 μl of the skin external preparations prepared from the above, respectively. The degree of the reaction represented on the skin in every time was scored by using the below experimental formula 1. The results are represented in Table 1.

Mean reaction degree=[{(reaction index×reaction degree)/(total number of the subject×the highest score (four point))}× 100]/times of the test       [Experimental Formula 1]

At this time, in the reaction degree, ± represents 1 score (point), + represents 2 score and ++ represents 4 score, When the mean reaction degree is less than 3, it is considered as being the safe composition.

for synephrine are 0.00, 0.00 and 0.00, respectively, and thus, it was determined that the unripe *Citrus unshiu* fruit extract and synephrine isolated from it are the safe material.

Example 10: Determination of Effect for Improving Atopy of Cream Comprising the Unripe *Citrus unshiu* Fruit Extract or Synephrine Isolated from It 10-1. Preparation of Cream Comprising the Unripe *Citrus unshiu* Fruit Extract or Synephrine Isolated from It Creams comprising the unripe *Citrus unshiu* fruit extract or synephrine isolated from it, having the ingredients and contents shown in below Table 2 were prepared. Specifically, aqueous phase, the purified water, triethanolamine and propylene glycol were heated to 70° C. to dissolve them, and then to it added the liquid in which oil phase, fatty acid, oily component, emulsifier and preservative were heated to 70° C. to dissolve them and stirred with homomixer (Tokushu Kika Ltd., Japan) to emulsify them. After the emulsifying them was completed, the said solution was cooled to 45° C., 0.03% by weight or 0.01% by weight of the unripe *Citrus unshiu* fruit extract or synephrine based on the total weight of the composition was added, dispersed and then cooled to 30° C.

TABLE 2

| Ingredient | Content (% by weight) |
|---|---|
| The unripe *Citrus unshiu* fruit extract | 0.03 or 0.01 |
| Carbomer 940 | 0.12 |
| Trehalose | 3.00 |
| Sorbitol | 1.00 |
| 1,3-Buthylene glycol | 5.00 |
| Bis-PEG-18 methyletherdimethylsilane | 1.00 |
| Glycerol | 4.00 |

TABLE 1

| Test material (ppm) | | 1st week | | | 2nd week | | | 3rd week | | | Mean reaction degree |
|---|---|---|---|---|---|---|---|---|---|---|---|
| | | 1st a/b/c | 2nd a/b/c | 3rd a/b/c | 1st a/b/c | 2nd a/b/c | 3rd a/b/c | 1st a/b/c | 2nd a/b/c | 3rd a/b/c | |
| Control | | —/—/— | —/—/— | —/—/— | —/—/— | —/—/— | 1/—/— | —/—/— | —/—/— | —/—/— | 0.09 |
| The unripe *Citrus unshiu* fruit extract | 1 | —/—/— | —/—/— | —/—/— | —/—/— | —/—/— | —/—/— | —/—/— | —/—/— | —/—/— | 0.00 |
| | 10 | —/—/— | —/—/— | —/—/— | —/—/— | —/—/— | —/—/— | —/—/— | —/—/— | —/—/— | 0.00 |
| | 100 | —/—/— | —/—/— | —/—/— | —/—/— | —/—/— | —/—/— | —/1/— | —/—/— | —/—/— | 0.09 |
| Synephrine | 10 | —/—/— | —/—/— | —/—/— | —/—/— | —/—/— | —/—/— | —/—/— | —/—/— | —/—/— | 0.00 |
| | 150 | —/—/— | —/—/— | —/—/— | —/—/— | —/—/— | —/—/— | —/—/— | —/—/— | —/—/— | 0.00 |
| | 300 | —/—/— | —/—/— | —/—/— | —/—/— | —/—/— | —/—/— | —/—/— | —/—/— | —/—/— | 0.00 |

(It is represented that a: ±, b: +, c: ++.)

As a result of the test, in the case of the control, the numbers of subjects belonging to ±, +, ++ are 1, 0, 0 in the 3rd patch of 2nd week, respectively, pastes for the remaining periods did not represent the reaction on the skin. In the case of unripe *Citrus unshiu* fruit extract, the skin external preparation comprising 100 ppm represented the skin reaction in 0, 1, 0 subject, respectively in the 1st paste in 3rd week, pastes for the remaining concentrations and periods did not represent the skin reaction, in the case of synerphrine of Example 2, all the test groups did not represent the skin reaction. As a result of calculating the result of the above Table 1 according to the Experimental Formula 1, the mean reaction degree for the control is 0.09, the mean reaction degrees for the unripe *Citrus unshiu* fruit extracts are 0.00, 0.00 and 0.09, respectively, and the mean reaction degrees TABLE 2-continued

| Ingredient | Content (% by weight) |
|---|---|
| Diel-pantenol | 0.30 |
| EDTA | 0.02 |
| Polysorbate 60 | 0.80 |
| Glycerol monostearate | 1.20 |
| Glycerol stearate/PEG-100 stearate | 0.90 |
| Sorbitan Sesquilatate | 0.30 |
| Lanette ® O | 1.60 |
| Cetyl ethylhexonoate | 3.00 |
| Caprilic/Carlic triglyceride | 1.00 |
| Cyclomethicone | 6.50 |
| Triethanol amine | 0.13 |
| Phenonip | 0.70 |
| Flavor, Preservative | Trace amount |

TABLE 2-continued

| Ingredient | Content (% by weight) |
| --- | --- |
| Purified water | Residual amount |
| Total | 100 |

10-2. Determination of the Effect for Improving Atopy of Cream Comprising the Unripe *Citrus unshiu* Fruit Extract or Synephrine Isolated from It Cream comprising 0.03 or 0.01% by weight of the unripe *Citrus unshiu* fruit extract or synephrine isolated from it, prepared according to the method of 10-1 as above was used for 30 children of atopy patients twice per day for 4 weeks. The control used the cream comprising the purified water instead of the unripe *Citrus unshiu* fruit extract or synephrine.

The effect improving atopy was determined by using Eczema Area Severity Index (EASI) score, the determination criterion was set as 5 for the case that there is no improvement of atopy, and 0 for the case that there are many improvements of atopy and the relative values were compared. The results are represented in Table 3.

TABLE 3

|  | Test period | | |
| --- | --- | --- | --- |
|  | 1st week | 2nd week | 4th week |
| Control | 2.85 | 2.57 | 2.28 |
| The unripe *Citrus unshiu* fruit extract | 2.74 | 148 | 0.69 |
| synephrine | 2.82 | 1.51 | 0.63 |

As a result of the experiment, when the cream comprising the unripe *Citrus unshiu* fruit extract or synephrine was used, it was observed that EASI score was reduced compared to the control, as the used period was longer, EASI score was reduced in proportion to the period, and thus, it was identified that it has the effective efficacy for atopy inflammation.

Preparation Example 1: Preparation of Cosmetics 1-1. Preparation of Cream

Cream comprising, as an effective ingredient, the unripe *Citrus unshiu* fruit extract or Synephrine, as indicated in Table 4 as below, was prepared according to the convention method.

TABLE 4

| Ingredient | Content (% by weight) |
| --- | --- |
| The unripe *Citrus unshiu* fruit extract or synephrine | 0.03 or 0.01 |
| Carbomer 940 | 0.12 |
| Trehalose | 3.00 |
| Sorbitol | 1.00 |
| 1,3-Buthylene glycol | 5.00 |
| Bis-PEG-18 methylether dimethylsilane | 1.00 |
| Glycerol | 4.00 |
| Diel-pantenol | 0.30 |
| EDTA | 0.02 |
| Polysorbate 60 | 0.80 |
| Glycerol monostearate | 1.20 |
| Glycerol stearate/PEG-100 stearate | 0.90 |
| Sorbitan Sesquilatate | 0.30 |

TABLE 4-continued

| Ingredient | Content (% by weight) |
| --- | --- |
| Lanette ® O | 1.60 |
| Cetyl ethylhexonoate | 3.00 |
| Caprilic/Carlic triglyceride | 1.00 |
| Cyclomethicone | 6.50 |
| Triethanol amine | 0.13 |
| Phenonip | 0.70 |
| Flavor, Preservative | Trace amount |
| Purified water | Residual amount |
| Total | 100 |

1-2. Preparation of Toner

Toner comprising, as an effective ingredient, the unripe *Citrus unshiu* fruit extract or Synephrine, as indicated in Table 5 as below, was prepared according to the conventional method.

TABLE 5

| Ingredient | Content (% by weight) |
| --- | --- |
| The unripe *Citrus unshiu* fruit extract or synephrine | 0.03 or 0.01 |
| Disodium EDTA | 0.01 |
| Aminocort | 1.00 |
| DL-pantenol | 0.10 |
| Trehalose | 0.10 |
| Glycerol | 3.00 |
| Carbopol EDT 2020 | 0.07 |
| Alcohol | 3.00 |
| Bis-PG-18 methyl ether dimethyl silane | 0.20 |
| Phenyl trimethicone | 0.10 |
| PEG-40 hydrogenated costol oil | 0.15 |
| Methylparabene | 0.05 |
| Triethanolamine | 0.13 |
| Phenonip | 0.70 |
| Phenoxyethanol | 0.50 |
| Flavor, Preservative, pigment | Trace amount |
| Purified water | Residual amount |
| Total | 100 |

1-3. Preparation of Lotion

Lotion comprising, as the effective ingredient, the unripe *Citrus unshiu* fruit extract or Synephrine, as indicated in Table 6 as below, was prepared according to the conventional method.

TABLE 6

| Ingredient | Content (% by weight) |
| --- | --- |
| The unripe *Citrus unshiu* fruit extract or synephrine | 0.03 or 0.01 |
| Carbomer 941 | 0.05 |
| Alantoin | 3.00 |
| HerbX hyaluron | 1.00 |
| Methylparaben | 0.10 |
| Glycerol | 1.10 |
| Disodium EDTA | 0.05 |
| Polysorbate 60 | 1.00 |
| Solitan Sesquiolate | 1.00 |
| Stearic acid | 1.00 |
| Glycerol stearate/PEG-100 stearate | 1.50 |
| Cetyl alcohol | 1.30 |
| Propylparabene | 0.05 |
| Buthylparabene | 0.05 |
| Macadamia oil | 0.05 |
| Demethicone | 0.05 |
| Caprylic/Capric Tryglyceride | 1.00 |
| Mineral oil | 4.50 |
| Triethanolamine | 0.10 |
| Phenoxyethanol | 0.50 |

TABLE 6-continued

| Ingredient | Content (% by weight) |
| --- | --- |
| Flavor | Trace amount |
| Purified water | Residual amount |
| Total | 100 |

Preparation Example 2: Preparation of Pharmaceutical Preparation 2-1. Preparation of Tablet In order to prepare a table comprising, as the effective ingredient, the unripe *Citrus unshiu* fruit extract or synephrine, ingredients of the below Table 7 were mixed and then pressed according to the conventional method to prepare the tablet.

TABLE 7

| Ingredient | Content (mg) |
| --- | --- |
| The unripe *Citrus unshiu* fruit extract or synephrine | 20 |
| Lactose | 20 |
| Starch | 20 |
| Magnesium stearate | 0.5 |

2-2. Preparation of Capsule

In order to prepare a capsule comprising, as the effective ingredient, the unripe *Citrus unshiu* fruit extract or synephrine, ingredients of the below Table 8 were mixed and then filled into the gelatin capsule according to the conventional method of the capsule to prepare the capsule.

TABLE 8

| Ingredient | Content (mg) |
| --- | --- |
| The unripe *Citrus unshiu* fruit extract or synephrine | 20 |
| Lactose | 20 |
| Starch | 20 |
| Magnesium stearate | 0.5 |

2-3. Preparation of Ointment

In order to prepare an ointment comprising, as the effective ingredient, the unripe *Citrus unshiu* fruit extract or Synephrine, ingredients of the below Table 9 were mixed and then prepared the ointment according to the conventional method of the ointment to prepare the ointment.

TABLE 9

| Ingredient | Content (g) |
| --- | --- |
| The unripe *Citrus unshiu* fruit extract or synephrine | 0.02 |
| Diethanolamine | 1.5 |
| Starch polyvinylpyrrolidone | 5 |
| propyleneglycol | 30 |
| Add the distilled water to make 100 ml | |

The invention claimed is:

1. A method of treating atopic dermatitis, psoriasis or eczema in a human in need thereof consisting essentially of administering therapeutically effective amounts of an unripe *citrus unshiu* extract, wherein the extract is prepared by using a solvent selected from the group consisting of propanol, acetone, ethyl acetate, chloroform, butylene glycol, and a mixture thereof.

* * * * *